(12) United States Patent
Bause et al.

(10) Patent No.: US 12,144,749 B2
(45) Date of Patent: Nov. 19, 2024

(54) METHOD FOR PRODUCING AN ORTHOPEDIC DEVICE AND ORTHOPEDIC DEVICE

(71) Applicant: Ottobock SE & Co. KGaA, Duderstadt (DE)

(72) Inventors: Ingrid Bause, Sonnenstein (DE); Thomas Bertels, Duderstadt (DE); Sebastian Betz, Göttingen (DE); Sarah Bierbaum, Göttingen (DE); Lukas Brünjes, Göttingen (DE); Hendryk Engelbart, Göttingen (DE); Lars Benjamin Finke, Landolfshausen (DE); Martin Hillman, Duderstadt (DE); Christian Müller, Kalefeld (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 668 days.

(21) Appl. No.: 17/282,734

(22) PCT Filed: Sep. 5, 2019

(86) PCT No.: PCT/EP2019/073754
§ 371 (c)(1),
(2) Date: Apr. 2, 2021

(87) PCT Pub. No.: WO2020/069817
PCT Pub. Date: Apr. 9, 2020

(65) Prior Publication Data
US 2022/0031480 A1   Feb. 3, 2022

(30) Foreign Application Priority Data

Oct. 4, 2018  (DE) ......................... 102018124516.5
May 29, 2019 (DE) ......................... 102019114458.2

(51) Int. Cl.
*B33Y 80/00* (2015.01)
*A61F 2/50* (2006.01)
(Continued)

(52) U.S. Cl.
CPC .............. *A61F 2/80* (2013.01); *A61F 2/5046* (2013.01); *A61F 2/7812* (2013.01); *B33Y 80/00* (2014.12)

(58) Field of Classification Search
CPC ........ B29C 64/106; A61F 2/5044; A61F 2/80; A61F 2/5046; A61F 2/7812; B33Y 80/00; B29L 2031/7532
See application file for complete search history.

(56) References Cited

U.S. PATENT DOCUMENTS 6,358,453 B1    3/2002  Slemker
2005/0119777 A1  6/2005  Arbogast et al.
(Continued)

FOREIGN PATENT DOCUMENTS

CN    104684510 A    6/2015
DE    102016201002 B4  7/2017
(Continued)

OTHER PUBLICATIONS

Japan Patent Office, "Office Action," issued in connection with Japan Patent Application No. 2021-516873 dated Jun. 20, 2023 (11 pages) (6 pages of English Translation and 5 pages of Original Document).
(Continued)

*Primary Examiner* — Monica A Huson
(74) *Attorney, Agent, or Firm* — HOLLAND & HART LLP

(57) ABSTRACT

The invention relates to a method for producing an orthopedic device, particularly a prosthesis liner, characterized in that the orthopedic device is produced at least partially by
(Continued)

means of an additive manufacturing process from at least one production material that is introduced into a support material in a flowable state and then hardens.

22 Claims, 9 Drawing Sheets

(51) Int. Cl.
*A61F 2/78* (2006.01)
*A61F 2/80* (2006.01)

(56) References Cited

U.S. PATENT DOCUMENTS

| | | |
|---|---|---|
| 2011/0009787 A1 | 1/2011 | Pallari |
| 2011/0161058 A1 | 6/2011 | Schottdorf |
| 2012/0095571 A1 | 4/2012 | Gunnarsson et al. |
| 2014/0188251 A1 | 7/2014 | Mosler et al. |
| 2015/0250624 A1 | 9/2015 | Mosler et al. |
| 2015/0328840 A1 | 11/2015 | Zachariasen |
| 2016/0067918 A1 | 3/2016 | Millar |
| 2016/0235560 A1 | 8/2016 | Cespedes et al. |
| 2017/0143519 A1 | 5/2017 | Muller |
| 2017/0246013 A1 | 8/2017 | Erenstone |
| 2017/0333223 A1 | 11/2017 | Rasmussen |
| 2018/0235779 A1 | 2/2018 | Dudding |
| 2022/0226129 A1* | 7/2022 | Finke ............... B33Y 80/00 |

FOREIGN PATENT DOCUMENTS

| | | |
|---|---|---|
| DE | 102017106903 B3 | 7/2018 |
| WO | 2017136405 A1 | 8/2017 |

OTHER PUBLICATIONS

Hajash, Kathleen et al., "Large-Scale Rapid Liquid Printing," 3D Printing and Additive Manufacturing, 4, 3 [Sep. 2017]: 123-132.
International Search Report issued in International Application No. PCT/EP2019/073754 on Dec. 13, 2019, 3 pgs.
Hinton et al. (2016), "3D Printing PDMS Elastomer in a Hydrophilic Support Bath via Freeform Reversible Embedding," ACS Biomater. Sci. Eng. 2016, 2. 1781-1786.
Wikipedia "Continuous Liquid Interface Production," Jan. 19, 2024, https://de.wikipedia.org/wiki/Continuous_Liquid_Interface_Production.
European Patent No. 19765698.6, Notice of Opposition dated Aug. 13, 2024; 39 pgs.; No. English translation of the Notice was provided. This application is related to the present application by priority; references cited in this Notice not previously submitted are provided in this submission.

* cited by examiner

METHOD FOR PRODUCING AN ORTHOPEDIC DEVICE AND ORTHOPEDIC DEVICE

CROSS-REFERENCE TO RELATED APPLICATIONS

This is a national phase application of International Application No. PCT/EP2019/073754, filed 5 Sep. 2019, which claims the benefit of German Patent Application No. 102018124516.5, filed 4 Oct. 2018; and also claims the benefit of German Patent Application No. 102019114458.2, filed 29 May 2019, the disclosures of which are incorporated, in their entireties, by this reference.

TECHNICAL FIELD

The invention relates to a method for producing an orthopedic device, particularly a prosthesis liner. The invention also relates to an orthopedic device that is or can be produced according to such a method.

In the present case, an orthopedic device is understood particularly to mean orthoses and prostheses and their components. Orthopedic shoes, shoe inserts and similar devices are also considered to be an orthopedic device.

Orthopedic devices have been known within the scope of the prior art for many years, and are produced and sold in a variety of different configurations for a wide range of applications. A variety of different materials are used, which take into account the different requirement profiles of the respective orthopedic device. For example, a prosthesis socket is produced for a leg prosthesis into which an amputation stump, such as an upper leg stump, is introduced. The prosthesis socket must have sufficient mechanical stability and strength to be able to withstand the sometimes enormous stresses and to guarantee that the wearer of the prosthesis feels secure when standing and comfortable at the same time. The net weight of the prosthesis socket should also be as low as possible, thereby further increasing the level of comfort. Nowadays, such prosthesis sockets are usually made of a carbon fiber composite material, which has a very high degree of mechanical strength at a low net weight. A prosthesis liner is often used as an interface between the prosthesis socket and the amputation stump, said liner being made of a cushioning and elastic material, such as a silicone or polyurethane. This is pulled over the amputation stump like a stocking before the amputation stump with the prosthesis liner is inserted into the prosthesis socket.

While today prosthetic sockets are usually custom-made for the patient and moulded from the amputation stump in one of several known methods, the prosthesis liner is usually made in standard sizes because its elasticity allows it to adapt to individual conditions.

BACKGROUND

The prosthesis itself is arranged on a residual limb and fixed to it. Various systems are available for fixing purposes; one fixing system provides for the so-called vacuum socket technology, in which the volume between the residual limb and an inner prosthesis socket wall is evacuated in the mounted state. For sealing and cushioning purposes, the prosthesis liner can be arranged on the residual limb, wherein said liner usually has a closed distal end and a proximal entry opening and surrounds the residual limb. A volume is formed between an outer side of the prosthesis liner and an inner side of the prosthesis socket by inserting the residual limb treated with the prosthesis liner; said volume is evacuated, thus creating a frictional connection between the prosthesis socket and the prosthesis liner. The prosthesis liner sticks to the prosthesis stump via adhesive forces, so that the prosthesis socket and the components attached to the prosthesis socket are fixed to the patient's residual limb. To achieve a permanent fixation of the prosthesis socket, it is necessary to seal the volume between the prosthesis liner and the prosthesis socket against the atmosphere. For this purpose, so-called caps or cuffs are provided which are pulled over the proximal edge of the prosthesis socket and rest on the outside of the prosthesis liner or residual limb so that no air can enter the gap between the proximal edge of the prosthesis socket and the prosthesis liner or residual limb. As an alternative to a cuff or even a cap, sealing lips can be arranged or fixed on the outside of the liner or on the inside of the prosthesis socket to effect a seal of a volume.

The prosthesis socket is usually made of a dimensionally stable material in order to have sufficient stability and strength to arrange further prosthesis components on it and to provide a support function for the soft tissue components of the amputation stump. The proximal edge of the prosthesis socket is designed to be as high as possible to be able to safely accommodate the amputation stump. In the case of a lower leg socket, for example, the proximal edge extends medially and laterally to the knee condyles and features deep cut-outs in the tibia and popliteal area. A similar construction occurs with a lower arm socket. In the case of an upper leg socket, a lateral elevation is designed to provide lateral stability.

The invention aims to to specify an improved production method for a variety of different orthopedic devices.

The invention solves the task by means of a method for producing an orthopedic device, particularly a prosthesis liner, characterized in that the orthopedic device is produced at least partially by means of an additive manufacturing process from at least one production material that is introduced into a support material in a flowable processing state and then hardens.

In addition to various 3D printing processes, additive manufacturing processes also include, for example, a three-dimensional printing process developed by the MIT which was published under the key term "rapid liquid printing". In this case, the object to be produced is generated in a container filled with a gel suspension or another material which does not react chemically with the production material, but serves exclusively to mechanically support the production material for as long as it has not yet hardened or sufficiently cross-linked. The gel suspension in this case is the support material. With all of these methods, the production material is processed in a flowable form, for example liquid. With the example of "rapid liquid printing", the production material in liquid or gel form, both of which are considered flowable, is introduced into the gel suspension at the desired positions by means of a positioning device, for example a nozzle that can be moved three-dimensionally. Due to the density ratios between the production material and the support material of the gel suspension as well as the high viscosity of the support material, the introduced production material remains in the respective position. In this way, three-dimensional objects can be "printed" by introducing the production material into the gel suspension at the desired position and in the desired shape, where it is then cross-linked, solidifies or hardens. The term "hardening" in the following also includes cross-linking or other reactions or changes in the properties of the production material which lead to an increase in dimensional stability or the achievement of a desired condition of the orthopedic device or component. In the case of flexible or elastic materials in particular, the flexibility or elasticity remains intact after hardening. Cross-linking is understood as hardening within the meaning of the invention. The advantage in comparison to conventional 3D printing processes lies, among other things, in the large number of possible production materials, including silicones that cross-link at room temperature and are available on the market. Another advantage is that the process using gel suspension makes it possible to position three-dimensional objects directly in a working space of the printer and not have to build them up layer by layer. Furthermore, the method allows for high production speeds and therefore low production costs.

Production materials include, for example, silicones and polyurethanes, but also thermoplastic materials, casting resins or other plastics. For a production material, it is only important that it can be processed and hardened in an applicable form, i.e. flowable, for example liquid or otherwise sprayable.

In this way, for example, prosthesis liners, prosthetic gloves, insoles and other orthopedic devices can be produced from conventional silicone easily, quickly and, if necessary, individually shaped. If thermoplastic materials are used, the mechanical stability and hardness resulting from hardening may be sufficient to produce, for example, prosthesis sockets, joint protectors or stiffening elements, such as splints for orthopedic devices, in this way using this method. Prosthesis coverings and cosmeses can also be produced in this way. In addition, test prostheses, such as test sockets or test cosmeses, can also be produced.

By using the additive manufacturing process, it is particularly easy to produce, for example, a cosmesis, in particular a foot cosmesis, an ankle cuff or, for example, an individually manufactured patella or an individual knee cap with or without a socket connection. In this way, such an orthopedic device can be designed, for example, to be waterproof and/or with a functionalization, for example with increased mobility by way of a bellows structure in the wrist area of a prosthetic hand.

SUMMARY

In a preferred configuration, the production material is supported during hardening and/or held in its position in a working space by the support material. It is preferably a self-hardening material or a material which can be hardened by increasing the temperature. When using a self-hardening material, it is advantageous that no influence by means of other hardening agents, for example electromagnetic radiation or chemical additives, is necessary. These advantages are also achieved when using a material that can be hardened by increasing the temperature, said material hardening via the application of thermal radiation, for example.

In addition to the production material that is introduced into the support material in a flowable state, fibers, especially continuous filaments, can also be introduced. They can be applied at the same time as the production material and in particular enclosed by it. The fibers contain or preferably are carbon fibers, which reinforce the component to be produced.

The production material is preferably composed of at least two components. It is preferable if a mixing ratio of the at least two components in relation to each other is adjustable. It is especially preferable if the mixing ratio can be adjusted during the additive manufacturing process. This configuration renders it possible, for example, to apply the production material in several components, each of which is in a flowable state. In this case, each of the components is preferably designed in such a way that a hardening does not occur or does so only very slowly. However, if the two components do come into contact with each other, a chemical reaction can be induced that creates the actual production material, which preferably hardens quickly. By changing the mixing ratio, the physical and/or chemical properties of the production material produced in this way can be influenced, so that the part of the orthopedic device produced in this manner exhibits almost infinitely different physical properties and can contain corresponding gradients.

In a preferred configuration, the production material is designed in such a way that, for example, it exhibits a Shore hardness after hardening whose value depends on the mixing ratio. In this way, areas with a high degree of hardness and areas with a low degree of hardness can be produced in one piece directly next to each other and against each other in a single process step without having to change the device or the material used. It is sufficient to only change the mixing ratio of the at least two components, which can be done during the additive manufacturing process.

This preferably enables a continuous variation of a material parameter or a physical property of the production material by way of a continuous variation of a mixing ratio. For example, a lower leg liner is conceivable which is designed to be considerably more elastic in the popliteal fossa area than in other areas. Alternatively or additionally, components with complex gradients in terms of wall thickness can be realized, which cannot be produced or can only be produced with considerable effort using manufacturing processes from the prior art and the corresponding mould construction required, for example.

In a preferred configuration, at least two different production materials are used in the additive manufacturing process. This preferably happens simultaneously. Here, the two different production materials differ in at least one property. For example, the production material can be used in different colors to create desired optical effects and aesthetic impressions. By using, for example, a colored production material, markers can also be added on or in the orthopedic device to be produced, or at least on a component of the orthopedic device that is at least partially produced with the additive manufacturing process. This is practical, for example, if the orthopedic device is to be worn in a particular orientation on the body of the wearer. For instance, if the prosthesis liner has integrated electrodes for picking up, for example, myoelectric signals from the amputation stump or stimulating the muscles of the amputation stump with electrical signals or treating plasma, it is important that the electrodes are reproducibly arranged at the right point of the respective amputation stump. Of course, this also applies for electrodes arranged on an orthosis that is pulled over an intact body part of the patient. By using markers, it is easier for the patient in these cases to mount the orthopedic device, for example the prosthesis liner, in the right orientation on the body part. These markers can be produced with the method according to this embodiment example of the present invention particularly easily by using the production material of the additive manufacturing process coloured in a different colour at the point where the marker is to be arranged.

By using production materials in two different colors, it is possible to produce a wear indicator or damage indicator. If, for example, only the production material in a first colour is visible from the outside of an intact orthopaedic device, the appearance of a second colour gives a clear signal that, for example, a wear part needs to be replaced or that the orthopedic device has a defect.

The at least two different production materials preferably differ in their electrical conductivity. For example, while a conventional silicone or polyurethane is electrically insulating, the addition of corresponding additives, such as soot particles or metal shavings, can render it electrically conductive. DE 10 2017 126 465, which has not been prepublished, describes corresponding devices whose base body is made of an electrically insulating material which can be made, for example, from the first production material by means of the additive manufacturing process. Said base body contains an electrical conductor with a core composed of an electrically conductive elastomer, which comprises an electrically insulating coating. This electrically insulating coating in the form of a parylene coating, for example, acts as a bonding agent between the conductor of the electrically conductive elastomer and the base body material. However, in the configuration of the present invention, the base body material in the form of the first production material and the electrically conductive elastomer material of the electrical conductor in the form of a second production material can preferably be processed at the same time. In a preferred configuration, both the material of the electrical conductor and the material of the base body, i.e. both production materials described here, are a silicone. As a result, the elastic properties of the first production material, which forms the base body in the example of an embodiment described, are not influenced by the electrical conductor. A bonding agent layer is not necessary, as both production materials harden at the same time. This results in an optimal bonding between the two production materials.

Therefore, with the method described here, at least one electrical conductor, but preferably more than one of the electrical conductors, can be arranged in the production material of the orthopedic device.

Alternatively or additionally, the production materials used differ in their hardness and/or their elasticity, for example, after hardening. The different production materials can be used at different points of the orthopedic device so that, for example, in the case of a prosthesis liner, the parts where a bone is positioned very close to the outside of the amputation stump and which require special cushioning can be covered with a particularly soft and cushioning material. If the prosthesis liner is, for example, a prosthesis liner for lower leg amputees, the popliteal fossa area can be made with an especially elastic production material in order to cope with the strong mechanical stresses caused by frequent stretching. Furthermore, by using a production material with a low degree of elasticity within a production material with a higher degree of elasticity, it is possible to create stiffeners to, for example, increase the longitudinal stiffness of a prosthesis liner while retaining lateral extensibility. Moreover, it is possible with the additive manufacturing process to create an auxetic structure as described in DE 10 2017 106 903 and used for prosthesis liners. Auxetic materials have negative Poisson's ratios. This means that, unlike with conventional materials, an extension of the material in one direction does not lead to a shortening in a second direction perpendicular to this direction; rather, an extension also occurs in this direction. In particular, two-dimensional auxetic materials can be used advantageously in liners. With the production method described here, the necessary structures can be produced, even in large quantities, in an especially simple and cost-effective manner.

If the different production materials are used for different areas of the orthopedic device or a component of the orthopedic device produced using the additive manufacturing process, the different production materials can also be used one after the other. In this case, a device with which the additive manufacturing process is conducted preferably comprises several outlets, which are preferably connected to various production material containers, such that the different production materials can be used immediately one after the other and/or simultaneously.

Preferably, the at least one production material is bonded to a separately produced component of the orthopedic device during the additive manufacturing process. To this end, the separately produced component, which may be, for example, a connection cap, a connection adapter made of another material, such as metal, an electrode, a battery holder or any other element, is arranged in the device and inside the support material in which the additive manufacturing process is conducted. With the "rapid liquid printing" method, the respective separately produced component is thus arranged inside the gel suspension. The production material for the additive manufacturing process is then positioned during the additive manufacturing process in such a way that it comes into contact with the respective separately produced component, thereby creating an integrally bonded connection between the separately produced component and the production material during the hardening of the production. Of course, the production material can also be arranged in such a way that, alternatively or additionally, a positive-locking connection is created after the production material has hardened. Alternatively or additionally, it is possible to introduce separately produced components into the already printed, but not yet hardened, production material. For example, after a prosthesis liner has been produced according to the described method, cables or stiffening threads or the like can be positioned in its walls, which then connect with the hardening production material in an integrally bonded or positive-locking manner.

A prosthesis liner often features a so-called liner cap in its distal area by means of which a mechanical connection to the prosthesis socket can be established. Electronic components, sensors, pneumatic, hydraulic or other elements can also be arranged in the liner cap. The liner cap is manufactured separately and can be bonded to the production material as a separately produced component during the additive manufacturing process. The same applies for electronic components, such as sensors, electrodes or other elements. These are also to be considered as separately produced components.

In a preferred design of the method, at least one object is introduced into the support material, wherein the production material is printed onto said object during the additive manufacturing process. The production material is then introduced in a flowable state into the support material in such a way that it comes into contact with the object introduced into the support material. An integrally bonded and/or positive-locking connection between the introduced object and the hardened production material preferably occurs during the hardening of the production material. It is thus possible to introduce a part of an orthopedic device made of elastic material, such as a prosthesis socket, into the support material and subsequently print padding and/or cushions onto it in the additive manufacturing process. The padding or cushions are at least partially, but preferably entirely, made of the production material. This material is introduced in a flowable state into the support material in such a way that it comes into contact with the prosthesis socket, which is also arranged in the support material.

This method is especially advantageous if a precise fit between two components is necessary or desired. In this way, a prosthetic, i.e. the plastic casing surrounding the actual prosthesis, can be printed directly onto the prosthesis, for example. In this way, a prosthetic hand, for example, or another orthopedic device can be introduced into the support material, for example immersed. The part of the orthopedic device to be produced in the additive manufacturing process can then be directly printed onto the immersed component. During the additive manufacturing process, functions such as individual damping properties can also be created. A prosthetic foot and/or a prosthetic foot casing that surrounds the actual prosthetic foot can be made, for example, of different production materials at different points, thereby resulting in different damping properties.

In addition, prosthesis liners in particular, but not only these orthopedic devices, often feature a textile layer or other textile components. If this is the case, this textile element can also be considered a separately produced component and bonded with the production material during the additive production process.

Orthoses often serve to apply a pressure on particular points of the body in order to support joints, for example, or to relieve ligaments or tendons. To this end, pressure pads are preferably used, which are often made of a silicone and arranged on the body of the wearer by way of the orthosis in such a way that, for example, pressure is applied to the desired point after closing an additional strap. Such a pressure pad can also be produced from a production material by way of a method of the kind described here, wherein the production material is preferably bonded with the separately produced component, for example the textile base body of the orthosis.

As previously explained, components and elements that are to be in contact with the production material may already be incorporated into the support material when the production material is applied in the flowable state. However, in the case of flexible elements such as textiles, this is only possible to a limited extent, as they exhibit little or no dimensional stability. It has thus been proven to be advantageous to produce, for example, a liner or a part of another orthopedic device as a closed volume. A support material is then provided in the interior of this volume. Due to the resistance caused by the enclosed support material, it is now particularly easy to apply a textile layer to the liner formed in this way without having to make a mould or a tool. Once the textile layer is applied, the liner can be opened at the proximal end and the support material within removed. The applied textile layer can be glued on beforehand, for example. In addition or alternatively to the application of textiles or other materials, it is advantageous in certain situations to mould another component, such as a prosthesis socket, directly on the liner. In this case, it is also advantageous if the liner can offer resistance to a load, which can be achieved in particular in the ways mentioned above.

To enhance to the effect of the enclosed support material, the resistance created by the support material, especially in the case of water-based support material, can be increased by freezing the closed part of the orthopedic device in which the support material is enclosed. As a result, the support material becomes hard and is able to absorb the forces acting during the application and especially the gluing of the textile layer without deforming the now cooled and frozen liner, which is preferably still closed. As an alternative to the closed variant of the part of the orthopaedic device produced by the additive manufacturing process, there can also be an inlet and/or outlet, in particular with or without a valve, through which, for example, the contained support material can be removed from the otherwise closed part of the orthopedic device. If a higher degree of dimensional stability of this part is desired, a medium, for example air, can be introduced into the otherwise closed part of the orthopedic device through a tube that is connected to the inlet, thereby building up the required pressure. Once the textile layer has been applied, the closed part of the orthopedic device can be opened and any support material contained within removed.

Alternatively or additionally, stiffening elements can be introduced into the otherwise closed part of the orthopedic device which are designed to be brought in particular into contact with each other by removing or discharging fluid from the volume, or at least to reinforce the contact between them via the removal or discharging. In a very simple example of an embodiment, said elements may be a granulate, for example sand. In this case, for example, if air is removed or discharged from the volume filled with the stiffening elements, i.e. the granulate, the individual stiffening elements come into contact or reinforce this contact with each other. This allows a rigid shape to form that supports the surrounding and/or contained orthopedic device.

In the additive manufacturing process, the wall thickness of the orthopedic device can be varied continuously or in discrete steps, thereby creating at least one protrusion, depression, thickening, taper and/or undercut.

It is advantageous if the additive manufacturing process produces an orthopdic device and/or component with at least one cavity. In principle, it is intended to create a cavity by printing around an area of the gel suspension with production material. Alternatively or additionally, however, a cavity can be produced by first applying the production material as a solid material, into which an auxiliary material is subsequently introduced while still in a liquid state, said auxiliary material forming the corresponding cavity. The auxiliary material can be a gas or a liquid, for example also the gel suspension used, and remain in the component after completion, for example to create an air cushion, or be removed again from the hardened component. The cavity, in particular the cavity produced in the manner described above, may exhibit different properties and perform a wide range of tasks. This cavity may be a closed cavity or comprise an opening or gap. For example, an openwork structure can be created that is honeycombed, for example, and serves to provide mechanical strength.

However, if the at least one cavity is a closed cavity, it can be used, for example, as an air cushion in order to cushion especially sensitive points of the body of the wearer of the orthopedic device, thereby increasing the level of comfort when worn. Air cushions produced in this way can also be designed with a connector, for example, for pumping air into or letting air out of the air cushion. As a result, it is possible to adjust the pressure inside the air cushion and, if necessary, the expansion of the air cushion, and to adapt it according to the individual needs. For example, variations in volume of an amputation stump can be accommodated. If, for example, an electrode is located on a side of the air cushion facing the body, the surface pressure with which the electrode is pressed against the skin of the wearer can be adjusted and optimized by way of such an inflatable air cushion.

With such an air cushion, pressure can also be applied over a large area and/or depending on the zone, which is necessary and advantageous, for example, for the treatment of scar tissue during the treatment of burns. Produced cavities may also be provided in the form of ducts that contain, for example, coolant in order to cool a body part that is in contact with the orthopedic device. Such ducts, which are produced as cavities from the production material in an additive manufacturing process, can also be used for transporting medicines.

Alternatively or additionally, the at least one cavity can be filled at least partially, but preferably completely, with at least one filling material during the additive manufacturing process, wherein preferably at least two cavities are filled with different filling materials. In the case of at least two cavities in particular, the two different filling materials, which are preferably already filled into the cavities during the additive manufacturing process, can be made of different components, such as a silicone, which chemically react with each other. Such a-b silicones are known from the prior art and lead to a hardening or cross-linking or stabilizing of the material as soon as the two components come into contact with each other. They can be used, for example, to fill a cavity that appears, for instance, between an amputation stump and a prosthesis liner when a standard-size liner is used and thus individually adapt the inner contour of the liner to fit the body shape of the wearer of the orthopedic device. The mixed yet still liquid material flows encapsulated in an already hardened shell as a liquid intermediate layer around the residual limb without coming into direct contact with it. It assumes the respective geometry of the residual limb and then hardens in this shape.

A device for carrying out such a method therefore features at least three dispensing nozzles through which the various materials can be dispensed. While the production material is introduced into the desired shape, for example into the gel matrix, from one dispensing nozzle, the different filling materials are introduced into the resulting cavities from the other dispensing nozzles. If the two filling materials are later to be reacted with each other, only a connecting wall located between the two cavities has to be separated.

Alternatively or additionally, the cavities are only filled once the production material has hardened. For example, DE 10 2018 111 442, which has not been pre-published, describes orthopedic devices, especially prosthesis liners, which feature cavities that are filled with a filling material following the hardening of the respective material that the walls of the cavity are made of. As a result, the mechanical stability at this point can be increased so that, for example, a support device or a support structure can be created inside the base body of the orthopedic device.

A corresponding design of the method described here renders it possible to also produce several components of the orthopedic device made of the at least one production material using the additive manufacturing process, wherein said components each feature a cavity, for example in the form of a tube or tunnel, and can therefore be joined with one another so that these various cavities come into contact and are bonded to each other, in particular fluidically. In this way, the cavities can be filled together with the respective structuring material. Of course, other materials, such as cooling or heat-emitting materials, can be introduced to heat or cool the orthopedic device, thereby increasing the level of comfort experienced by the wearer of the orthopedic device.

In a preferred configuration, the production material used in the additive manufacturing process is an elastic material when completely hardened. In this case in particular, but also with other production materials, it is advantageous to foam-fill a cavity created during the additive manufacturing process. To this end, a foaming material is introduced into the finished cavity which then foams and preferably completely fills the cavity. In principle, every foaming material known from the prior art can be used for this purpose, wherein multi-component materials in particular are used. In this case, at least two components of the foaming material are introduced into the cavity; they then react with one another and start to foam.

If the orthopedic device is, for example, a vacuum liner, i.e. a prosthesis liner where the prosthesis socket is held on the prosthesis liner by a negative pressure, i.e. by evacuating the gap between the prosthesis liner and the prosthesis socket, it is advantageous to integrate cavities in the sense of evacuation ducts into the orthopedic device, which in this case may be the liner and/or the prosthesis socket, in order to be able to produce the negative pressure as homogeneously as possible in the gap between the prosthesis socket and the prosthesis liner.

It is advantageous if at least one pneumatic element and/or at least one hydraulic element, preferably at least one volume reservoir, at least one sealing lip, at least one valve and/or at least one pump, is produced from the at least one production material by means of the additive manufacturing process, wherein the hydraulic and/or pneumatic element is preferably produced as one piece with another component of the orthopedic device. Such components are used in a range of orthopedic devices and, in this way, can be manufactured easily and cost-effectively as well as optimally positioned. A sealing lip, which is used for example in vacuum liners to seal the gap to be evacuated between the prosthesis liner and the prosthesis socket in an airtight manner to the outside, is usually arranged on the outer side of a prosthesis liner. It is also possible for several sealing lips to be arranged on the outer side and/or inner side of the prosthesis liner. In this case, the entire liner can be produced in an additive manufacturing process using the method described here, wherein the at least one production material is the material of the liner. This may refer, for instance, to a silicone or a polyurethane. In this case, the sealing lip can be produced at the same time as the rest of the liner during the additive manufacturing process, thereby achieving an optimum adhesion between the sealing lip and the base body of the liner, which is then produced by an integrally bonded connection. As an alternative, the sealing lip can also be subsequently arranged on an already complete base body of a liner which was manufactured separately. This is especially advantageous if a standard liner is used to treat the patient, but the optimum position of the sealing lip on the outer side of the liner depends, for example, on the length of the amputation stump and must therefore be individually adapted for the wearer of the orthopedic device. The individual adaptation may be achieved using the additive manufacturing process.

In a number of prosthesis liners, for example, an air line with a reed valve or with a one-way valve is used within the liner to use the lifting motion between the prosthesis liner and the prosthesis socket that occurs during walking to pump out and evacuate the volume. These pneumatic elements can be integrated into the base body of the liner, which can be produced from the at least one production material, with the method described here. US 2017/0143519 A1 relates to a prosthesis liner with a one-way valve and a poured-in, air-permeable material that forms a flow path. A pump chamber may be provided between an outer liner and an inner liner.

Similarly to a sealing lip, locking elements for the mechanical locking of two components of the orthopedic device to each other can also be moulded onto a separately or simultaneously manufactured component, for example the base body of a liner, by the additive manufacturing process, in particular by the rapid liquid printing method. The rapid liquid printing method is described in US 2018-281295 A1, for example.

In a preferred configuration, the method comprises an initial recording of measurement data from a patient, which is then made available to an electrical and/or electronic control system. This control system is configured to control the additive manufacturing process at least also on the basis of this measurement data. This is especially advantageous for orthopedic devices that are individually adapted to the patient. Prosthesis sockets and prosthesis liners in particular can be manufactured in this way quickly, easily, cost-effectively but still individually for each patient. Various methods for recording the measurement data are known from the prior art. For example, the body part of the patient that will come into contact with the orthopedic device is captured by an optical scanner and measured three-dimensionally. The measurement data detected in this way is made available to the electrical and/or electronic control system. In this case, the amputation stump or the body part to be measured can be introduced, mounted or inserted into a special device, so that pressure conditions which should be present with mounted prostheses or orthoses and which naturally influence the geometric shape of the body part and the amputation stump can be taken into account.

In addition to the described production of individually adapted orthopedic devices, the embodiments of the method described here also render the production of standardized shapes and/or sizes of orthopedic devices easier and more cost-effective than in the prior art, as there is no need to produce casting moulds. The production material is simply positioned inside the support material in the desired arrangement and distribution and then hardens or is hardened.

In addition, semi-individual configurations of orthopedic devices can be produced, in which, for example, digitally stored standard shapes are individualised by means of individual measurements taken from the patient. These can then be easily and quickly produced by means of the additive manufacturing process. In this way, for example, a position and/or size of a sealing lip on the outer side of a prosthesis liner can be adapted on a patient-by-patient basis. Prosthetic gloves, for example, can also be customized in terms of length and/or width, while otherwise standard dimensions are used.

In preferred embodiments of the method described here, the feel or structure, for example, of the orthopedic device or the component of the orthopedic device to be produced with the additive manufacturing process can be influenced and, if necessary, amended in particular areas. It is thus possible, for example, to produce a prosthesis liner which exhibits a different feel or structure in the proximal area than in the distal area. This can make it easier to put on the device, for example. The adhesive properties can also be varied by, for example, at least partially, but possibly also completely, applying a surface structure to the inside of a prosthesis liner that is produced by the additive manufacturing process. Due to the previously mentioned evacuation ducts for a negative pressure supply to a prosthesis liner, the negative pressure distribution in a negative pressure liner can also be individually adjusted and optimally selected to make it more comfortable for the patient to wear. To this end, evacuation ducts are integrated into the orthopedic device, which is preferably done during the additive manufacturing process. The volume can be evacuated by way of these evacuation ducts, wherein the negative pressure distribution is individualized via the shape and design of the ducts.

Specifically, the use of different production materials also allows, for example, a Shore hardness of the respective hardened production material to be selected. In this way, it is also possible, for example, to produce a wear-resistant outer layer and a soft, cushioning core material at the same time by using two different production materials. In addition, the production material can be arranged in a foam-like structure, allowing the creation of a breathable wall.

The orthopedic device is preferably a prosthesis liner for use in a prosthesis socket, wherein the prosthesis socket comprises an accommodation space with a distal end and a proximal edge. The accommodation space is designed in such a way that the amputation stump treated with the prosthesis liner can be introduced into it and accommodated there. The method comprises the determination of a sealing lip course on an outer side of the prosthesis liner that corresponds to the course of a height contour of the prosthesis socket or on the basis of existing, known anatomical conditions of an amputation stump, and the arrangement of a sealing lip on the outer side of the prosthesis liner along the determined sealing lip course by means of the at least one additive manufacturing process. This also comprises the production of a liner or a liner base body to which the sealing lip is moulded as a single piece.

The height contour is the course of the proximal edge of the prosthesis socket in the proximal-distal direction and forms the course of the proximal end geometry of the prosthesis socket. After determining the height contour, a sealing lip course on the outer side of the prosthesis liner corresponding to the course of the height contour of the prosthesis socket is determined. A sealing lip is arranged on the outside of the prosthesis liner along the determined sealing lip course. This is achieved by means of the at least one additive manufacturing process.

The sealing lip course thus follows the height contour of the proximal edge of the prosthesis socket in the mounted state and is designed to correspond to the upper end geometry of the prosthesis socket. The position of the sealing lip on the prosthetic liner is determined so that the sealing lip is arranged distally to the proximal edge of the prosthesis socket when the prosthesis liner mounted on the amputation stump is fully inserted into the prosthesis socket. Due to the corresponding course of the sealing lip to the proximal end geometry of the prosthesis socket, it is possible to arrange the sealing lip in such a way that it extends as far as possible proximally when the prosthesis liner and the prosthesis socket are mounted, wherein the volume to be evacuated between the prosthesis liner and the prosthesis socket is larger compared to the designs in the prior art. This increases the force with which the prosthesis socket is held to the prosthesis liner without having to reduce the pressure within the evacuated volume compared to embodiments of the prior art. At the same time, the force required to hold the prosthesis socket on the prosthesis liner is distributed over as large an area as possible and thus evenly on the amputation stump.

The geometry that is individually adapted to the proximal edge of the prosthesis socket and a corresponding course of the sealing lip maximize the mechanical quality of the interface and reduce the stresses on the residual limb, in particular the amputation stump. This makes it more comfortable for the user and establishes a secure connection between the prosthesis socket and the residual limb. The course of the sealing lip can be determined, for example, on the basis of an existing or calculated course of the proximal edge of a prosthesis socket, in particular in digital form. The known course of the proximal edge of the prosthesis socket serves as a reference for the course of the sealing lip, which is determined accordingly. The determination of the course of the sealing lip can also be based on a scanned residual limb or data obtained in another way about the shape and/or condition of the residual limb or its anatomical features. The digitally available or calculated anatomy can serve as the basis for the prosthesis liner to be manufactured and also for the prosthesis socket to be manufactured. The prosthesis liner and, if necessary, the prosthesis socket are digitally modelled around the model or digital image of the residual limb. The shape corresponds largely to the outer contour of the residual limb, with allowances for padding on the liner and, if necessary, adjustments for the prosthesis socket for relief areas or compression areas to compensate for variations in volume. The prosthesis liner can also only be designed using only the residual limb model or the digital image of the residual limb and/or the prosthesis socket and converted into a digital data set, wherein the course of the sealing lip can be determined based on the anatomical conditions without a pre-existing or calculated prosthesis socket data set.

In an embodiment of the invention, the height contour of the proximal edge of the prosthesis socket is detected before determining the course of the sealing lip. The height contour, i.e. the course of the proximal edge of the prosthesis socket in the proximal-distal direction, forms the course of the upper end geometry of the prosthesis socket. In addition to detecting a height contour of an already physically available prosthesis socket, for example via a scanning method, moving a height sensor along the proximal edge or parallel thereto and assigning the height data to the circumferential coordinates, or by a non-contact measurement, for example optical measuring methods or other scanning, the determination can also be made solely on the basis of data about a prosthesis socket, in particular a prosthesis socket that is yet to be produced. If a 3D model or a data set already exists on the basis of which the prosthesis socket is to be manufactured, the course of the sealing lip can be determined based on this data and a prosthesis liner manufactured.

The sealing lip is preferably arranged on the prosthesis liner at an offset in the distal direction to the proximal edge of the prosthesis socket to prevent the sealing lip from protruding proximally beyond the proximal edge of the prosthesis socket when the prosthesis liner is on and fully inserted. When detecting the height contour, preferably not only the course of the proximal edge of the prosthesis socket in the proximal-distal direction is determined, but also the distance of the height contour from the distal end of the accommodation space. From the distance determined in this way, it can be determined at what distance from a distal end of the prosthesis liner the proximal edge of the prosthesis socket will abut the prosthesis liner when the prosthesis liner has been inserted into the prosthesis socket on an amputation stump. Starting from this line, the sealing lip is preferably arranged distally at an offset on the prosthesis liner. The displacement or shift in the distal direction away from the proximal edge of the prosthesis socket creates a safety zone, by way of which, for example, deviations in the intended orientation of the prosthesis liner on the residual limb can be compensated.

The detection of the course of the height contour occurs in the proximal-distal direction and preferably takes into account the overall length of the prosthesis socket, and therefore also the distance of the sealing lip course from the distal end of the prosthesis liner. Alternatively or additionally, a circumferential contour of the proximal edge of the prosthesis socket is detected across the circumference. This renders it possible to adjust an extension of the sealing lip in the radial direction, i.e. a distance of the radially outer edge of the sealing lip to the outside of the prosthesis liner, to fit the respective patient. The extension of the sealing lip is preferably not constant across the circumference, but instead varies depending on the anticipated distance of the amputation stump and the outer side of the liner pulled over it from the inner side of the prosthesis socket.

The sealing lip is preferably arranged equidistantly to the proximal edge of the prosthesis socket in the proximal-distal direction across the circumference of the prosthesis liner, i.e. it extends at least essentially, but preferably completely identically to the height contour of the proximal edge of the prosthesis socket.

The sealing lip is preferably arranged in a sealing lip area which is wider in the proximal-distal direction than the sealing lip itself and represents a mounting area, within which the sealing lip can be arranged and fixed on the outer side of a pre-fabricated prosthesis liner. The sealing lip area serves to facilitate production and renders it possible, in the at least one additive manufacturing process, to arrange the sealing lip itself within a predetermined area in the proximal-distal direction on the outer side of the prosthesis liner. The proximal and distal border of the sealing lip area preferably depends on and, particularly preferably, corresponds to the height contour of the proximal edge of the prosthesis socket.

The sealing lip area is preferably twice as wide as the sealing lip at its transition to the outer side of the prosthesis liner, i.e. the base of the sealing lip arranged on the outer side of the prosthesis liner.

The height contour or the height contour and the circumferential contour of the prosthesis socket are preferably captured optically. The captured image data form, for example, a basis for a digital 3D model for which or from which a data set is created. On the basis of the 3D model data set, the course of the sealing lip or the course and shape of the sealing lip are determined depending on the captured height contour or the captured circumferential and height contour. The height contour can also be captured using existing data, such as a 3D model of the socket, without the need for a prosthesis socket to be physically present. For example, if a prosthesis socket is created in an additive or another manufacturing process using a data set of a limb stump, such as an amputation stump, the inner contour of the prosthesis socket essentially follows the outer contour of the stump, with an allowance for variations in volume and, where applicable, the material strength of the prosthesis liner.

If the prosthesis socket is not produced on the basis of digital data, for example data obtained from the residual limb itself or a plaster model thereof, the inner contour of an existing prosthesis socket is preferably captured optically or saved in a computer system. By comparing the outer contour of the residual limb and the inner contour of the prosthesis socket and the height contour of the proximal edge of the prosthesis socket, which is also available within the 3D model, the course of the sealing lip on the outer side of the prosthesis liner is determined. Of course, this also includes the position of the sealing lip on the outer side of the prosthesis liner. In addition, the height and shape as well as the thickness of the prosthesis liner or a base body of the prosthesis liner are preferably determined and processed as a data set for production in the at least one additive manufacturing process. Within the scope of the at least one additive manufacturing process, for example within the scope of a rapid liquid printing process, the prosthesis liner is produced with the course of the sealing lip and sealing lip height and/or sealing lip thickness adapted to the height contour and/or circumferential contour.

The course of the sealing lip can also be determined directly from anatomical data, for instance on the basis of a scan of a residual limb. The height contour and circumferential contour of the socket can then be determined either from the course of the sealing lip initially considered suitable or optimal, so that the course of the sealing lip serves as a reference for the course of the proximal edge of the prosthetic socket. Alternatively, the height contour and circumferential contour of the socket are also detected from the anatomical data of the scan. As a result, the course of the sealing lip corresponds to the course of the height contour of the prosthesis socket, irrespective of whether the course of the sealing lip is created and determined subject to the initially determined height contour of the prosthesis socket, the height contour of the prosthesis socket is created and determined subject to the initially determined course of the sealing lip, or the course of the sealing lip and the height contour are created and determined independently from one another on the basis of the anatomical conditions using, for example, the digital 3D model of the residual limb.

The height of the sealing lip can be determined as a function of a recorded distance between an inner side of the prosthesis socket and the outer side of the residual limb to be inserted, over which the base body of the prosthesis liner may have been pulled.

A prosthesis liner manufactured in this way preferably forms a system comprising a prosthesis socket and the prosthesis liner, in which the prosthesis socket comprises an accommodation space for a residual limb treated with the prosthesis liner. The prosthesis socket has a distal end and a proximal end. The proximal end of the prosthesis socket has a height contour and a circumferential contour. At least one sealing lip is configured or fixed on the outer side of the prosthesis liner facing the prosthesis socket, wherein the sealing lip course of the at least one sealing lip corresponds to the course of the height contour of the prosthesis socket when the prosthesis liner is fully inserted. The sealing lip does not have to be flush with the proximal edge of the prosthesis socket; rather, it is intended that the sealing lip is arranged on the prosthesis liner at an offset distally from the proximal edge of the prosthesis stem following the end contour.

The prosthesis socket is designed to have a closed wall distal to the at least one sealing lip in the fully inserted state of the mounted prosthesis liner in order to create an interface area with as large an area as possible so that a negative pressure can be generated over as large an area as possible, by means of which the required holding force is generated and transferred to the amputation stump.

The prosthesis socket is preferably designed to be dimensionally stable in order to ensure sufficient stability for the accommodation of the residual limb with the liner and the arrangement of further prosthesis components, such as prosthetic joints. The at least one sealing lip is fixed to or configured on a base body of the prosthesis liner and may exhibit an uneven height across the circumference of the prosthesis liner, i.e. it may protrude radially outwards from the outer side of the prosthesis liner to different extents, in order to compensate for variations or differences in shape between the outer contour of the residual limb and the inner contour of the prosthesis socket.

An embodiment of the invention proposes that the at least one sealing lip is fixed to or configured on a base body of the prosthesis liner and exhibits an uneven height across the circumference of the prosthesis liner, i.e. an uneven extension radially outwards from the outside of the prosthesis liner. As a result, differences in the radial distance between the outside of the base body in the mounted state and the inside of the prosthesis socket can be compensated. This ensures that the sealing lip always abuts the inner wall of the prosthesis socket when the residual limb is inserted with the liner. The height that differs across the circumference of the prosthesis liner, i.e. the different radial expansion, is detected, for example, by comparing the scanned inner side of the prosthesis socket and the scanned outer side or the 3D model of the residual stump.

The course of the sealing lip preferably does not lie in one plane and is therefore not straight, but describes a spatial curve with an irregular distance over the circumference to the distal end of the prosthesis liner or the prosthesis socket.

The prosthesis liner for a system described above comprises at least one sealing lip that is configured on or fixed to the outer side of the prosthesis liner, which forms a sealing lip course in the shape of a spatial curve. The sealing lip course of the at least one sealing lip is designed to correspond to the course of a height contour of a proximal edge of a prosthesis socket into which the prosthesis liner mounted on the residual limb is to be inserted.

The invention also solves the problem by means of an orthopedic device, especially a prosthesis liner, that can be or is produced according to one of the methods described above.

In the following, some examples of embodiments of the present invention will be explained in more detail by way of the attached figures:

BRIEF DESCRIPTION OF THE DRAWINGS

They show.

DETAILED DESCRIPTION

Figure 1:
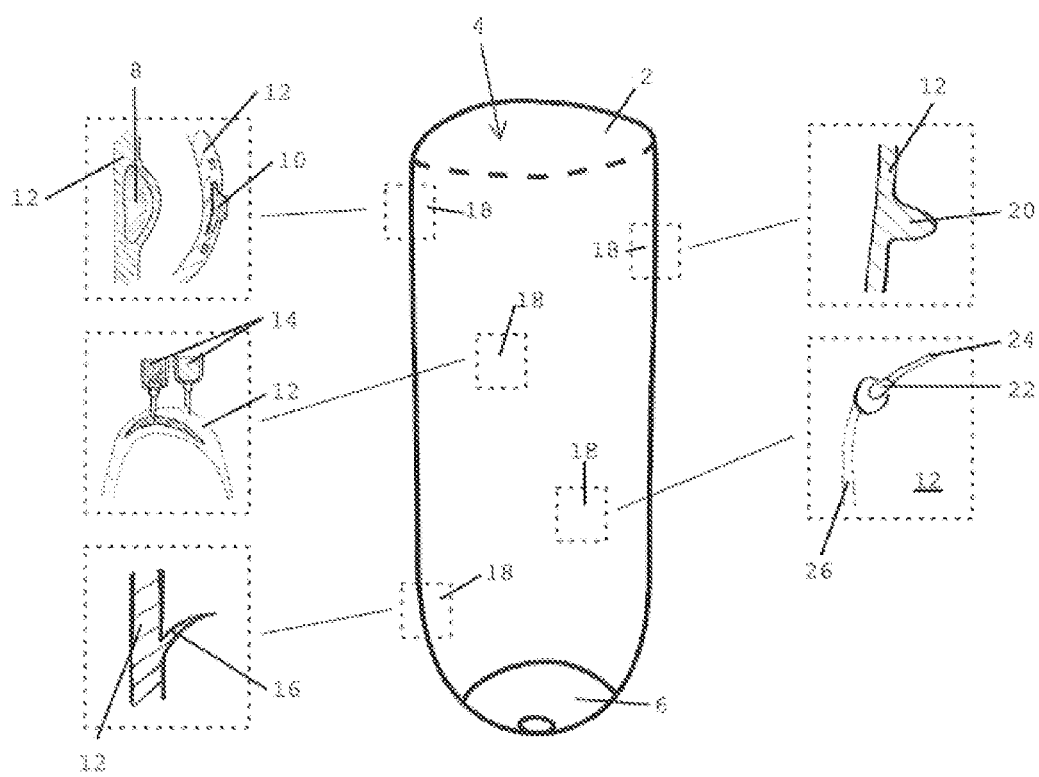
FIG. 1—the schematic representation of a prosthesis liner with various components,
FIG. 2—the schematic representation of a prosthesis liner with various design elements,
FIG. 3—the schematic representation of a prosthesis liner with various surface structures,
FIG. 4—the schematic representation of a prosthesis liner with various material structures,
FIG. 5—the schematic partial overview of components to be produced with the method according to an example of an embodiment of the present invention,
FIG. 6—the schematic representation of different manufacturing processes on measure,
FIG. 7—the schematic representation of a partial standard liner and a standard prosthesis liner,
FIG. 8—a individual representation of a prosthesis liner,
FIG. 9—a system composed of a prosthesis socket and a prosthesis liner arranged within it, and
FIG. 10—a schematic representation of a variation of the production method.

The middle area of FIG. 1 shows a prosthesis liner 2 which has been produced according to an example of an embodiment of the present invention. The prosthesis liner 2 features an opening 4 in the proximal area and a liner cap 6 in the distal area. The small sections, outlined with dashed lines, depict various components that can be arranged on the prosthesis liner 2.

At the top left, separately manufactured components in the form of, for example, a cushion 8 and an electrode 10, are depicted, which are enclosed by the base body of the prosthesis liner 2 and its production material 12 in the example of an embodiment shown. The box below contains a configuration in which two different production materials are processed simultaneously via two feeds 14. This renders it possible, for example, to integrate a production material with a higher degree of hardness as a stiffening element into a softer production material which is, for instance, a liner material for a base body of the prosthesis liner 2.

The bottom left-hand box contains a sealing lip 16, which may be designed, for example, to be a separately manufactured component onto which the production material 12 is printed with the additive manufacturing process. The base body of the liner 2 and the sealing lip 16 are preferably produced together in a single production step, namely the additive manufacturing process. Alternatively, the base body of the prosthesis liner 2 may be provided as a separately manufactured component, onto which the sealing lip 16 is printed. The small position boxes are merely intended to show by way of example that the components shown can be arranged in a wide variety of positions on the prosthesis liner 2.

The upper right-hand area in FIG. 1 shows that the production material 12 is provided in the form of a bulge 20, which may be a locking element, for example. This can also be easily produced using a method according to an example of an embodiment of the present invention. The bulge 20 may be designed as a separate component onto which the production material 12 is printed during the additive manufacturing process. Alternatively or additionally, a bulge 20 can also be made from the production material 12 or a second production material in the additive manufacturing process. The base body of the liner 2 and the bulge 20 are preferably produced together in a single production step, namely the additive manufacturing process.

The bottom right of FIG. 1 shows a connecting element 22 being printed onto the production material 12. Via such a connecting element 22, a cable 24, for example, can be connected to an electrical conductor 26 located inside the production material 12. Said conductor may be connected, for example, to an electrode, not depicted in FIG. 1.

Figure 2:
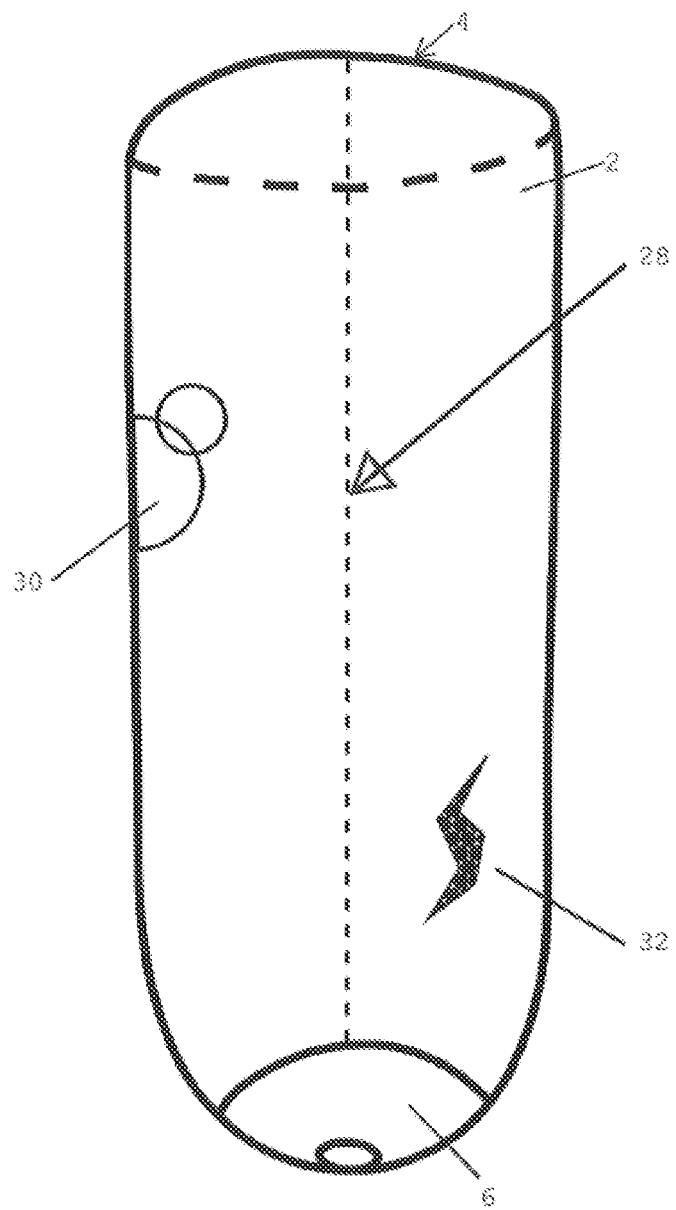

FIG. 2 depicts the prosthesis liner 2 with various optical elements, which can be produced using colored production materials 12 in the additive manufacturing process. A marker line 28 extends from the opening 4 to the distal liner cap 6, which serves to make it easier for the wearer of the orthopedic device to mount the orthopedic device, i.e. the prosthesis liner 2 in the example of an embodiment shown, in the correct orientation. Of course, it is not essential for the marker line 28 to extend from the proximal opening 4 to the distal liner cap 6.

A design element 30 is depicted in the left-hand area of the prosthesis liner 2, said element performing an essentially aesthetic function. For example, it may be designed as a logo which indicates that the orthopedic device comes from the manufacturer.

The third optical element is a wear indicator 32, which is also made of a colored production material. Such a wear indicator 32 can be realized, for example, by designing a base body of the prosthesis liner 2 to be multi-layered. This means that several production materials are used in the additive manufacturing process that differ at least in color. If the outer layer of the prosthesis liner 2 is defective or worn, the other color of the respective layer beneath becomes visible and acts as a wear indicator 32.

Figure 3:
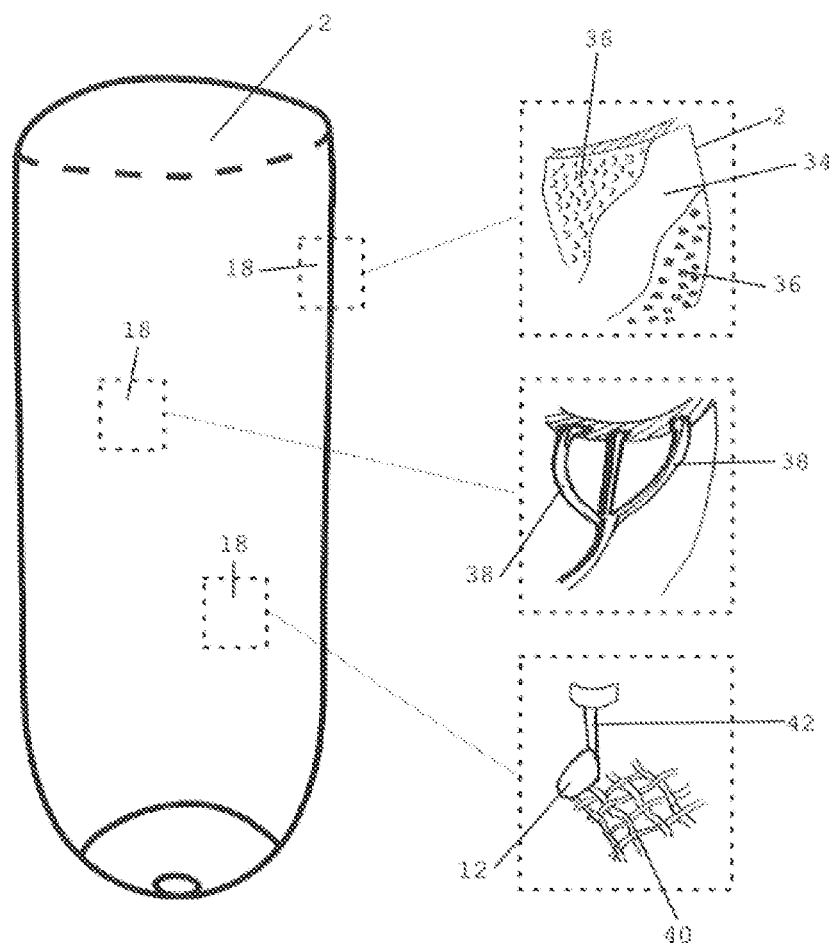

FIG. 3 shows the prosthesis liner 2 with three schematic position boxes 18, which again can only be examples for positions of different elements.

Various structures are indicated on the right-hand side. The top box depicts an outer side of the prosthesis liner 2, which features areas 34, 36 with different textures. While the middle area 34 has a smooth surface, the surface of the prosthesis liner 2 in the peripheral regions 36 is designed to be structured.

The box below contains evacuation ducts 38, which are integrated as groove-like structures into the side wall of the prosthesis liner 2 during the additive manufacturing process. They enable the evacuation of a negative pressure, which occurs between the prosthesis liner and a prosthesis socket, not depicted, when the prosthesis liner 2 is mounted.

The bottom area of FIG. 3 shows a textile layer 40 onto which the production material 12 is applied via an outlet nozzle 42 during the additive manufacturing process.

Figure 4:
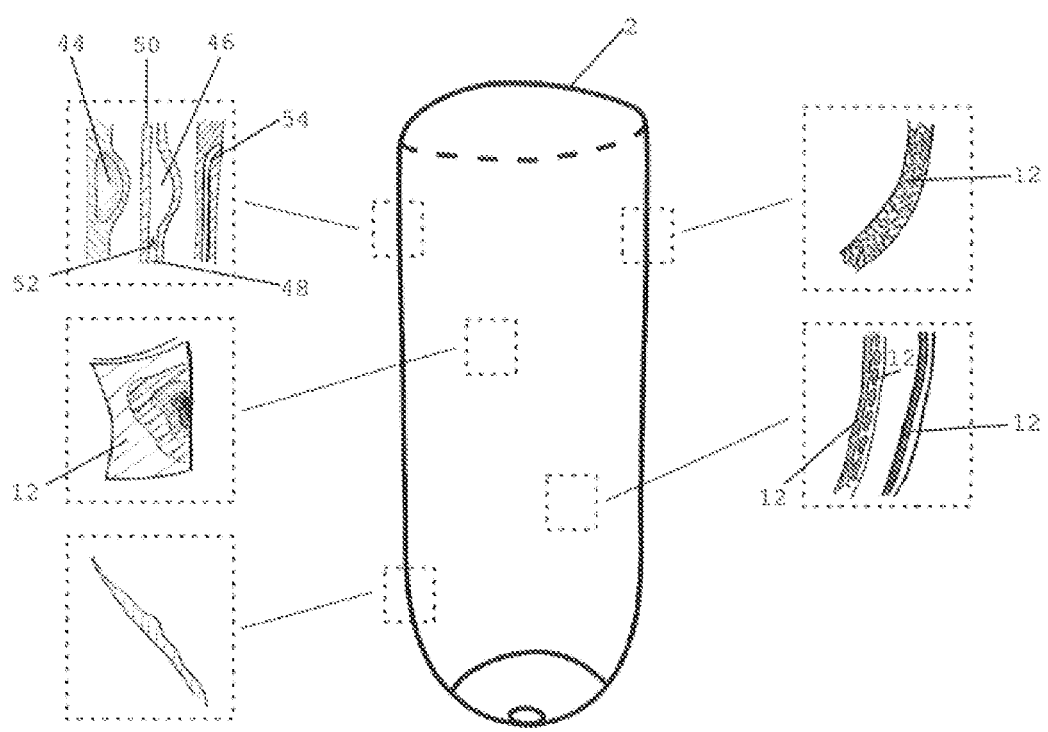

FIG. 4, on the other hand, depicts the prosthesis liner 2 with schematic representations of various material structures. The upper left-hand area of FIG. 4 contains various types of cavity, which can have different functions. A closed volume 44 is depicted at the far left, which acts as a padded cushion. The middle area, however, depicts a volume reservoir 46 that comprises an inlet 48 and an outlet 50. A reed valve 52 is located in the inlet 48, said reed valve acting as a one-way valve. The volume reservoir 46 with the inlet 48 and outlet 50 may form part of a hydraulic or pneumatic system, for example. The volume reservoir 46 as well as the inlet 48, outlet 50 and the one-way valve 52 can be made from the production material 12 during the additive manufacturing process. The right-hand area contains a duct 54 that can be used for cooling purposes, for example.

In the box below, it is schematically shown that different areas of the prosthesis liner 2, which may all be made of a production material 12, may have different Shore hardness levels. The bottom area depicts a cross-section of a side wall of the prosthesis liner 2. The different thicknesses that the liner may have at different points can be seen. The different thicknesses can be created continuously or in discrete steps with the additive manufacturing process.

In the upper box on the right-hand side of FIG. 4, it is schematically depicted that the production material 12 can be made, for example, in the form of a foam, such as a silicone foam. The box below contains so-called hybrid materials composed of different production materials 12. As shown in the left-hand section, this may be a positive-locking connection between the individual production materials 12, while in the right-hand section, several layers of different production materials are used that are joined to each other in an integrally bonded manner. The method according to the examples of embodiments of the present invention can be used to produce such hybrid materials in a single production step, namely the additive manufacturing process.

Figure 5:
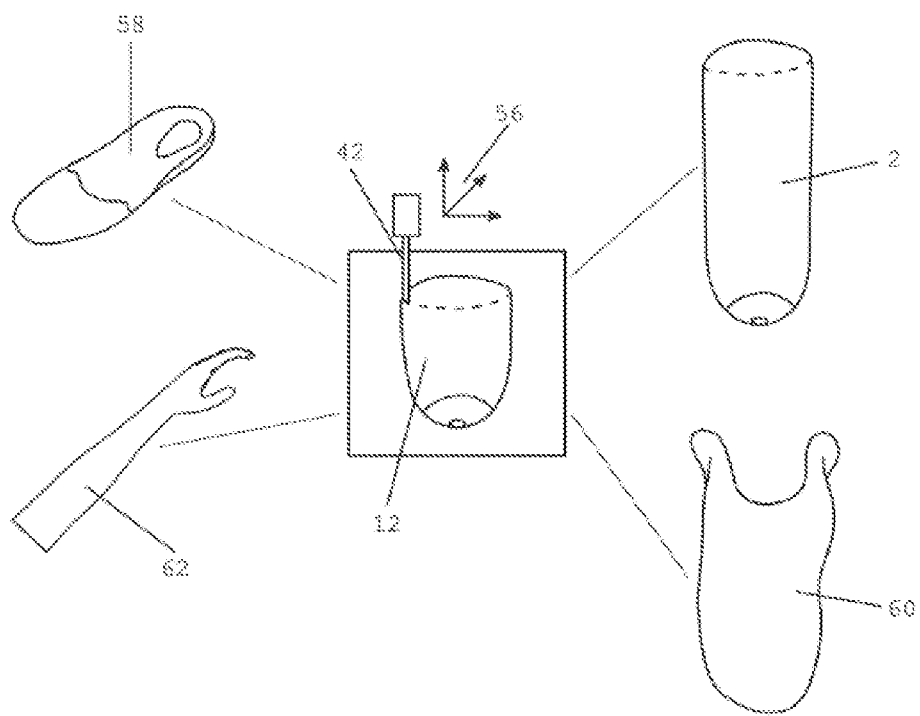

An additive manufacturing process is schematically depicted in the middle of FIG. 5, wherein the example of the embodiment shown relates to the rapid liquid printing method developed by MIT. The production material 12 is ejected through an outlet nozzle 42, which can be moved freely in all three spatial directions, as indicated by the arrows 56, and introduced into the support material at the desired position. The products arranged around the central area in FIG. 5 illustrate the variety of possible orthopedic devices that can be manufactured in this way. These are, for example, an insole 58, the prosthesis liner 2, a prosthesis socket 60 and a prosthetic glove 62, as used, for example, for encasing a prosthetic hand.

Figure 6:
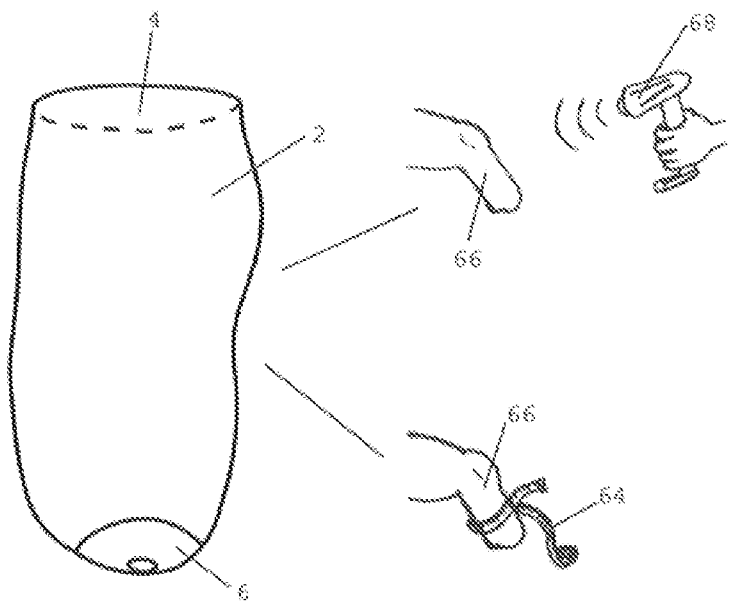

FIG. 6 schematically depicts that an individually shaped prosthesis liner 2 can be produced with a proximal opening 4 as well as a distal liner cap 6. This can be done, for example, by measuring an amputation stump 66 by means of a measuring tape 64 on the one hand, or another classical measuring method. Alternatively or additionally, the amputation stump 66 can be measured in a contactless manner by means of a scanner 68, as depicted in the upper section of FIG. 6. Irrespective of the measuring method used, the detected measurement data is supplied to an electrical and/or an electronic control system that controls the production device used for the additive manufacturing process.

Figure 7:
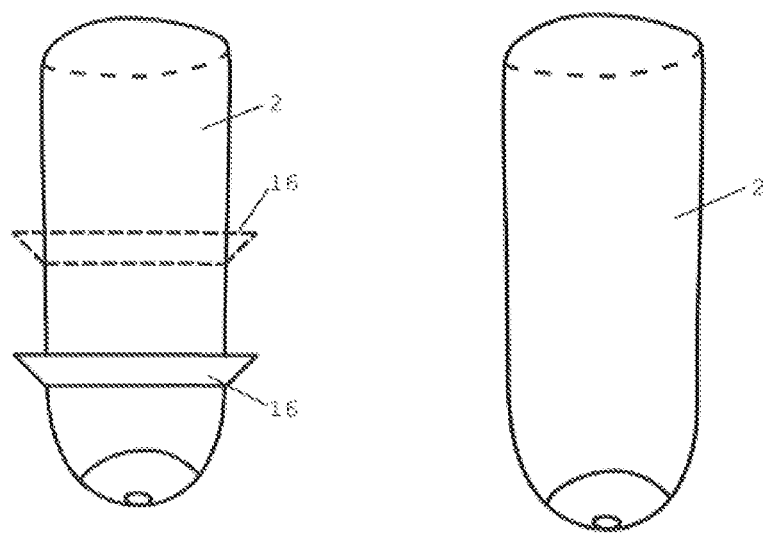

The right-hand area of FIG. 7 shows the known prosthesis liner 2, which has a standard size and shape. The prosthesis liner 2 is also shown in the left-hand area, on which a sealing lip 16 is now arranged. The sealing lip 16, depicted with dashed lines, schematically shows that this sealing lip can be arranged in different positions, differing on an individual basis, on the basic prosthesis liner 2.

Figure 8:
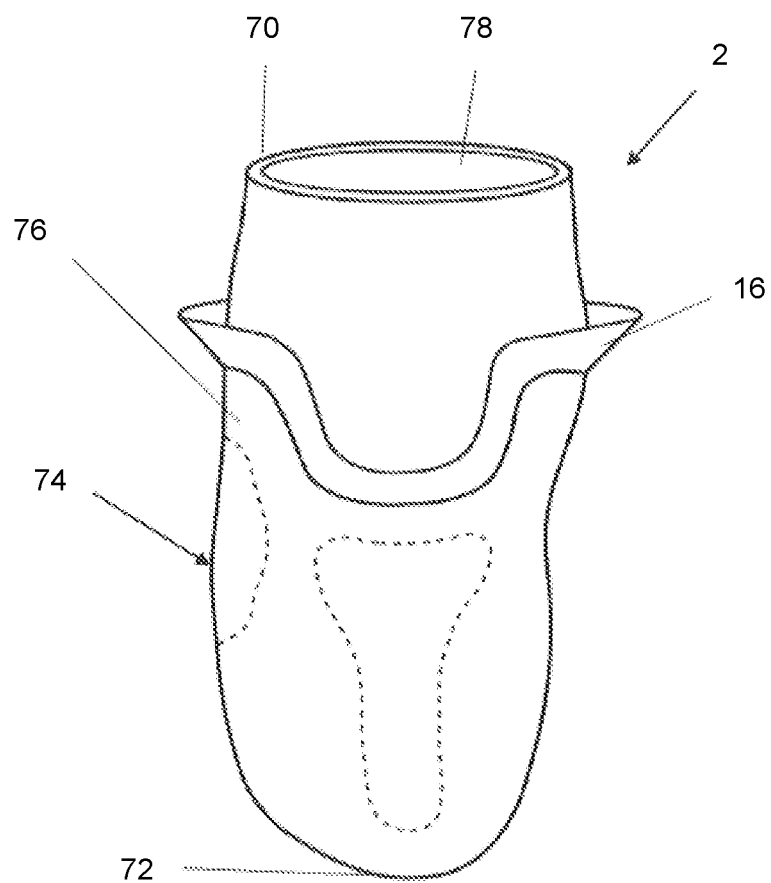

In an individual representation, FIG. 8 depicts a prosthesis liner 2 with a proximal edge 70 and a distal end region 72. The distal end region 72 is designed to be closed; the proximal edge 70 surrounds the circumference of an entry opening.

The prosthesis liner 2 has a base body 74 with an outer side 76 and an inner side 78. The base body 74 is designed to flexible and preferably elastic, at least in the circumferential direction. The inner side 78 of the base body 74 is preferably composed of an adhesive polymer, such as silicone. As an alternative, the inner side 78 can be completely and partially coated with an adhesive coating. The coating may be made, for example, of a silicone or another polymer that adheres to the skin. The outer side 76 of the base body 74 can also be made of an elastomer or be at least partially coated with an elastomer. It is also possible that a textile is applied to the outer side 76 to establish a uniformity of pressure in a gap between the prosthesis liner 2 and a prosthesis socket, which is not shown. Alternatively or additionally, elevations or ducts can be arranged on the outer side 76, for example configured or inserted or applied, so as to enable fluidic connections across the entire longitudinal extension, i.e. from distal to proximal, as well as around the circumference.

A sealing lip 16 is arranged on the base body 74 that forms a seal between the proximal and distal region of the prosthesis liner 2 after it has been inserted into a prosthesis socket, not depicted here. The sealing lip 16 can be made of an airtight material or coated in such a way that no air can pass through the sealing lip 16. For example, the sealing lip 16 can be made of a silicone or a polymer, or be coated with such a material. The sealing lip 16 is preferably produced as a single piece with the base body 74 as part of the at least one additive manufacturing process, for example via the rapid liquid printing method. The area distal to the sealing lip 16 on the outer side 76 of the base body 74 may be provided with a textured surface to allow pressure to be distributed in areas spaced apart from each other. The structuring can, for example, take the form of textile material that can be glued or laminated on, or via ducts and/or elevations on the outer side 76.

The sealing lip 16 protrudes radially from the base body 74 and is preferably designed to be elastic so that the outer side of the sealing lip 16, which faces away from the base body 74, rests on the prosthesis socket and presses against it. In the example of an embodiment shown, the sealing lip 16 is not designed to protrude vertically from the outer side 76 of the base body 74, but is designed or arranged to be inclined. The inner side of the sealing lip 16, which faces the base body 74, encloses an acute angle between them. In principle, it is also possible to provide a reverse orientation or to have the sealing lip 16 protrude vertically. When inserting the prosthesis liner 2 into a prosthesis socket, the sealing lip 16 is then usually folded over, resulting in an orientation in which the distally oriented side of the sealing lip 16 rests against the inner side of the prosthesis socket. If in the volume sealed by the sealing lip 16 between the prosthesis socket and the area distal to the sealing lip 16 there is a negative pressure compared to atmospheric pressure, the sealing lip 16 is pressed against the inner wall of the prosthesis socket, so that a self-reinforcing sealing effect occurs.

It can be seen from FIG. 8 that the proximal edge 70 of the prosthesis liner 2 is designed to be a straight line or arranged in one plane, the plane being essentially perpendicular to the longitudinal extension of the prosthesis liner 2. In contrast to this, the sealing lip 16 does not extend in a common plane, in particular not in a plane parallel to or inclined to the proximal edge 70 of the prosthesis liner 2, but along a spatial curve corresponding to the course of the height contour of the prosthesis socket at its proximal edge. The example of an embodiment depicted in FIG. 8 shows a prosthesis liner 2 for a lower leg. The tibial plateau is indicated by the broken line. The sealing lip 16 extends in the frontal area just above the tibial plateau and extends medially and laterally towards the proximal edge 70. In the rear part of the prosthesis liner, the sealing lip 16 can run lower again in the distal direction. Such a course corresponds to the course of the proximal edge of a lower leg socket, which runs deeper in the frontal tibia area and in the popliteal area, i.e. further in the distal direction than mediallateral. Medially and laterally of the knee joint, prosthesis socket areas can be arranged extending further in the proximal direction to achieve increased lateral stability and improved contact of the lower leg socket with the residual limb.

Figure 9:
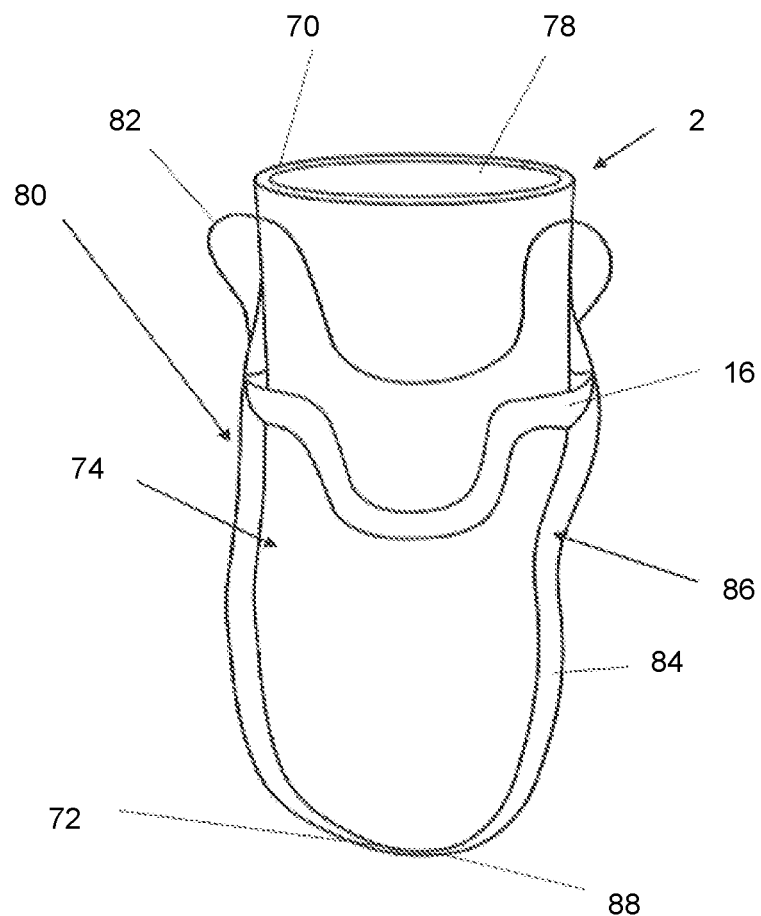

FIG. 9 features a schematic representation of the prosthesis liner 2 according to FIG. 8 after having been pulled on. The prosthesis liner 2 is mounted on the residual limb, not depicted here, and inserted into a prosthesis socket 80. The prosthesis socket 80 has a proximal edge 82 which does not lie in a flat plane, but describes a spatial curve. The prosthesis socket features medially and laterally raised areas which extend further in the proximal direction than the areas arranged frontally and in the popliteal fossa region. A cut-out can be seen at the front which allows the kneecap to move. A corresponding cut-out or depression is configured in the rear area of the popliteal fossa to allow for a flexion of the leg without the prosthesis socket with its dorsal region getting trapped between the rear thigh and the calf region.

The prosthesis liner 2 is fully inserted into an accommodation space 84 of the prosthesis socket 80, meaning that the distal end 72 of the prosthesis liner is situated in the region of the distal end 88 of the prosthesis socket 80: possibly, it lies or is arranged thereon slightly spaced from it, for example via padding. The sealing lip 16 rests on the inner wall of the prosthesis socket 80 and seals a volume 88 between the inner wall of the prosthesis socket 80 and the outer wall 76 of the prosthesis liner 2 distally to the sealing lip 16. The volume 86 is evacuated, for example, through an outlet valve by way of a pumping motion while walking or by a motor-drive pump, i.e. it is brought to a pressure level that is below the atmospheric pressure.

FIG. 9 shows that the course of the sealing lip corresponds to or follows the course of the proximal edge 82 of the prosthesis socket and is only located or arranged at an offset in the distal direction on the outer side of the base body 74. Ideally, the sealing lip 16 extends as close as possible to the proximal edge 82 of the prosthesis socket 80. In particular, the height course or height contour, i.e. the course of the sealing lip 16 around the circumference of the base body 74 in the proximal-distal direction, corresponds to the height course of the proximal edge 82 of the prosthesis socket Slight deviations may be possible, in particular the sealing lip course can be determined in an area which is essentially parallel to the course of the height contour of the proximal edge 82 of the prosthesis socket 80, the proximal and distal limits of the area being designed to correspond to the height contour course of the proximal edge 82.

The contour in the circumferential direction, i.e. the contour of the inner circumference of the prosthesis socket 80 in the area of contact of the sealing lip 16 can also be detected. The contour of the outer circumference of the sealing lip 16 can then be designed to correspond to the course of the circumferential contour in the area of contact of the outer sealing lip edge with the inside of the prosthesis socket 80, with an allowance so that the sealing lip 16 can rest against the inside of the prosthesis socket 80 with a slight pre-tension due to the restoring forces during deformation after insertion of the prosthesis liner 2 in the prosthesis socket 80.

Alternatively to a design of the prosthesis socket 80 as a lower leg socket with elevations on the medial and lateral side, a design, for example, as an upper leg socket may include an elevation on only one side laterally, extending approximately to the axis of rotation of the hip joint. Accordingly, a cut-out is designed on the medial side of the upper leg that is offset in the distal direction, so that a corresponding sealing lip course is created on an upper leg liner.

To produce such a liner 2, the height contour of the prosthesis socket 80, which is usually custom-made, is first captured. To this end, the height of the prosthesis socket 80 is also captured, i.e. the distance from the proximal edge 82 to the distal end 12 on the inside of the prosthesis socket 80 across the circumference of the residual limb. The shape and dimensions can preferably be captured optically, for example by image recording and image evaluation; alternative recording data such as scanning or traversing with measuring sensors can also be carried out.

Based on the captured course of the height contour of the proximal edge 82, it is then determined where the sealing lip 16 should rest against the inside of the prosthesis socket and thus where the sealing lip should be arranged on the outside 76 of the base body 74 of the prosthesis liner 2. The recorded data is used to create a 3D data model. The liner 2 is constructed on the basis of the data model of the prosthesis socket 80, for example with a standard base body 74 and an individual sealing lip course of the sealing lip 16, which is oriented to the course of the proximal edge 82 of the prosthesis socket 80. The shape of the prosthesis liner 2 with the adapted sealing lip course is also calculated as a 3D data model. The 3D data model is used to generate production data, which is used to produce the prosthesis liner 2 with the sealing lip profile corresponding to the profile of the proximal edge 82 of the prosthesis liner using the at least one additive manufacturing process.

Figure 10:
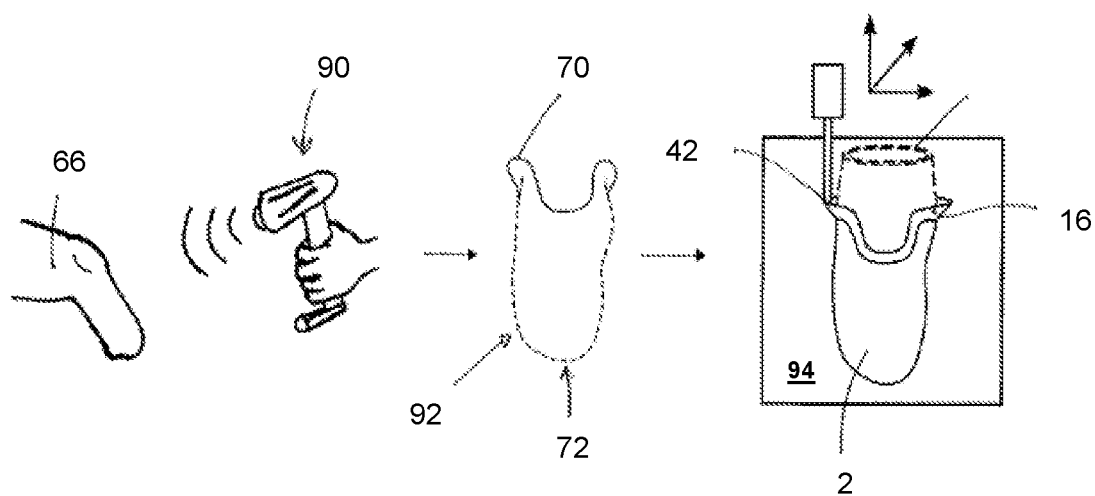

FIG. 10 shows a possible method for producing a prosthesis liner 2. The outer contour of an amputation stump 66, in this case a lower leg stump, is recorded, e.g. scanned, using an optical recording device 90. A 3D model of the amputation stump 66 is created and processed in a computer, not depicted. The 3D model is used to calculate a data set 92 that at least essentially represents the shape of the subsequent prosthesis liner 2. In addition to the course of the sealing lip, the data set 92 also defines the outer contour of the prosthesis liner 2, in particular also the distal end region 72 as well as the material thickness of the prosthesis liner 2. Via the data set 92 it is possible to define reinforcements, material weaknesses as well as the use of different materials which are then used or incorporated during the manufacturing process. The actual prosthesis liner 2 can be manufactured on the basis of the data set 92. In the example of an embodiment shown, the proximal edge 70 or the course of the proximal edge 70 of the actual prosthesis socket 2 in space is not yet depicted as defined in the data set 92. The remaining contour of the prosthetic liner 2 is indicated by the broken line. The data set 92 or the basic scan data can be used to create a data set for the prosthesis socket 80, which forms the basis for its manufacture, for example in an additive manufacturing process. The course of the sealing lip in space is defined as a contour line and can serve as a reference for the course of the contour of the proximal edge 82 of the prosthesis socket 80. The sealing lip course of the sealing lip 16 on the outside of a prosthesis liner 2 still to be manufactured can therefore be determined first, and then the prosthesis socket 80 is designed. Conversely, it is possible to adapt the sealing lip to an already defined contour of the proximal edge 82 of a virtual or existing prosthesis socket 80.

Using the data set 92, the prosthesis liner 2 is manufactured using an additive manufacturing process. In the example of an embodiment shown, production is carried out according to the so-called rapid liquid printing method, in which a support material 94 is arranged in a tank or storage container. Via an outlet nozzle 42, which can be moved three-dimensionally in space, the material of the prosthesis liner 2 is introduced into the support material 94 and the prosthesis liner 2 is produced by means of additive manufacturing. The dashed line indicates the proximal end contour of the prosthesis liner 2, which is straight in the example of an embodiment shown. The proximal end contour or edge 70 of the prosthesis liner 2 may also correspond to the course of the sealing lip 16 or to the proximal edge 82 of the prosthesis socket 80.

REFERENCE LIST 2 prosthesis liner
4 opening
6 liner cap
8 cushion
10 electrode
12 production material
14 feed
16 sealing lip
18 position box
20 bulge
22 connecting element
24 cable
26 electrical conductor
28 marker line
30 design element
32 wear indicator 34 middle area
36 peripheral zone
38 evacuation duct
40 textile layer
42 outlet nozzle
44 closed volume
46 volume reservoir
48 inlet
50 outlet
52 reed valve
54 duct
56 arrow
58 insole
60 prosthesis socket
62 prosthetic glove
64 measuring tape
66 amputation stump
68 scanner
70 proximal edge
72 distal end region
74 base body
76 outer side
78 inner side
80 prosthesis socket
82 proximal edge
84 accommodation space
86 volume
88 distal end
90 optical recording device
92 data set
94 support material

The invention claimed is:

1. A method for producing a prosthesis liner characterized in that the prosthesis liner is produced at least partially by means of an additive manufacturing process from at least one production material that is introduced into a support material in a flowable state and then hardens, wherein the prosthesis liner is configured to be pulled over an amputation stump of a user before the prosthesis liner is inserted into a prosthesis socket.

2. The method according to claim 1, characterized in that the production material is supported during hardening by the support material and/or held in its position in a working space.

3. The method according to claim 1, characterized in that the production material is composed of at least two components.

4. The method according to claim 3, wherein a mixing ratio of the at least two components can be adjusted during the additive manufacturing process.

5. The method according to claim 1, characterized in that at least two different production materials are used simultaneously in the additive manufacturing process.

6. The method according to claim 1, characterized in that the at least one production material is bonded with a separately produced component of the prosthesis liner during the additive manufacturing process.

7. The method according to claim 1, characterized in that, in the additive manufacturing process, the wall thickness of the prosthesis liner is varied continuously or in discrete steps, thereby creating at least one protrusion, depression, thickening, taper and/or undercut.

8. The method according to claim 1, characterized in that a prosthesis liner with at least one cavity is created with the additive manufacturing process.

9. The method according to claim 8, characterized in that the at least one cavity is at least partially filled with at least one filling material during the additive manufacturing process.

10. The method according to claim 1, characterized in that at least one pneumatic element and/or at least one hydraulic element is produced from the at least one production material by means of the additive manufacturing process, wherein said element is produced in one piece with another component of the prosthesis liner.

11. The method according to claim 1, characterized in that measurement data is recorded from a patient and made available to an electrical and/or electronic control system, which is configured to control the additive manufacturing process at least on the basis of the measurement data.

12. The method according to claim 1, wherein the prosthesis socket comprises an accommodation space with a distal end and a proximal edge, the method comprising the following steps:
   a) determining a sealing lip course on an outer side of the prosthesis liner that corresponds to the course of a height contour of the prosthesis socket or on the basis of existing, known anatomical conditions of an amputation stump, and
   b) arranging a sealing lip on the outer side of the prosthesis liner along the determined sealing lip course by means of the at least one additive manufacturing process.

13. The method according to claim 12, characterized in that the sealing lip is arranged on the prosthesis liner at an offset in the distal direction to the proximal edge of the prosthesis socket.

14. The method according to claim 12, characterized in that the height contour of the prosthesis socket is captured optically, a digital 3D model is created, and the sealing lip course is determined depending on the recorded height contour.

15. A prosthesis liner that is produced by a method according to claim 1.

16. The method according to claim 2, wherein the production material includes a self-hardening material or a material which can be hardened by increasing the temperature.

17. The method according to claim 4, characterized in that the production material exhibits a Shore hardness after hardening whose value depends on the mixing ratio.

18. The method according to claim 9, wherein the at least one cavity is completely filled with at least one filling material during the additive manufacturing process.

19. The method according to claim 18, wherein, wherein at least two cavities are filled with different filling materials during the additive manufacturing process.

20. The method according to claim 10, wherein the at least one pneumatic element and/or at least one hydraulic element comprises at least one volume reservoir, at least one sealing lip, at least one valve and/or at least one pump.

21. The method according to claim 10, wherein the at least one pneumatic element and/or at least one hydraulic element is produced as a single component in a single processing step with another component of the orthopedic device.

22. The method according to claim 13, wherein the sealing lip is arranged on the prosthesis liner equidistant in the distal direction to the proximal edge of the prosthesis socket.

* * * * *